United States Patent [19]

Milco

[11] Patent Number: 5,624,546
[45] Date of Patent: Apr. 29, 1997

[54] METHOD AND APPARATUS FOR THE DETECTION OF TOXIC GASES

[75] Inventor: Gary A. Milco, Fremont, Calif.

[73] Assignee: Mil-Ram Technology, Inc., San Jose, Calif.

[21] Appl. No.: 534,597

[22] Filed: Sep. 27, 1995

Related U.S. Application Data

[63] Continuation of Ser. No. 296,452, Aug. 26, 1994, abandoned.

[51] Int. Cl.⁶ ........................... G01N 27/26
[52] U.S. Cl. ........................ 205/779.5; 205/780.5; 205/782.5; 205/785.5; 205/786; 205/793; 205/794.5; 204/412; 204/415; 204/431; 204/432; 422/83; 422/88; 422/98
[58] Field of Search .................... 204/415, 412, 204/431, 432, 425; 422/83, 88, 98; 205/779.5, 780.5, 782.5, 785.5, 786, 793, 794.5

[56] References Cited

U.S. PATENT DOCUMENTS

| | | | |
|---|---|---|---|
| 4,076,596 | 2/1978 | Connery et al. | 204/415 |
| 4,176,032 | 11/1979 | Stevenson, Jr. | 204/415 |
| 4,563,249 | 1/1986 | Hale | 204/415 |
| 4,853,091 | 8/1989 | Mund et al. | 204/431 |
| 5,344,546 | 9/1994 | Kiesele et al. | 204/415 |

OTHER PUBLICATIONS

T.M. Florence, Anodic Stripping Voltammetry with a glassy carbon electrode mercury plated in situ, J. Electroanal. Chem. 27(1970) 273–281.

*Primary Examiner*—Bruce F. Bell
*Attorney, Agent, or Firm*—Robert Charles Hill

[57] ABSTRACT

A compact electrochemical cell utilized for the detection of numerous toxic gases. The cell includes working and counter electrodes, surrounded by a liquid electrolyte, all of which is enclosed behind a gas permeable, hydrophobic membrane. The working electrode may be a single electrode or may be composed of multiple glassy carbon electrodes arranged in a planar electrode array. The counter electrode is either spatially separated from the array or comprises one or more electrodes in the array. The electrolyte composition varies with the type of gas to be detected and can be aqueous, partially aqueous, or substantially non-aqueous. The electrolyte includes an alkali metal halide. A fixed potential applied between the working and counter electrodes is sufficient to initiate electrochemical reactions in the presence of the gas to be detected without interfering reactions of the electrolyte or air.

24 Claims, 4 Drawing Sheets

METHOD AND APPARATUS FOR THE DETECTION OF TOXIC GASES

This is a continuation of application Ser. No. 08/296,452 filed on Aug. 26, 1994, now abandoned.

BACKGROUND OF THE INVENTION

1. Field of the Invention

The present invention relates to a method and apparatus for detecting gases and more specifically to an electrochemical cell suitable for detecting numerous toxic gases. The device is suitable for both stationary and portable monitoring.

2. Background Information

The requirement for monitoring toxic gases in the environment has steadily increased in recent years as safety and health professionals have become increasingly aware of the dangers posed by these substances. Greater awareness has further prompted government regulations to address environmental monitoring and related issues. Although such monitoring serves to protect the environment as a whole, the safety of people in the workplace continues to be of most vital concern. In this regard, most toxic gases have various levels or limits, typically set by industry associations or regulatory agencies. Typically, several levels are defined for each type of gas. For example, a threshold limit value (TLV) sets the maximum allowable level of a gas that a person may be exposed to for an eight-hour period, five days a week. The short-term exposure limit (STEL) gives the maximum exposure that a person may be exposed to for a fifteen minute period not to exceed four occurrences per 8-hour work day. The permissible exposure limit (PEL) is the maximum limit a person may be exposed to the gas for any time period. Adherence to these standards requires a toxic gas detector capable of accurate detection of the toxic gases of interest. Further, as these various exposure limits may span a large range of concentrations, the toxic gas detector must accurately measure the concentration over a wide range of concentrations.

Several electrochemical gas sensing devices are now commercially available and used extensively in industry for the primary purpose of safeguarding the work place environment. Unfortunately, these devices are largely based on a common design and therefore share in their shortcomings. Specifically, most available devices are based on fuel cell technology. In general, these devices operate by providing a working electrode and a counter electrode, with an electrolyte disposed between the electrodes. A gas of interest present in the ambient diffuses through a membrane into the electrolyte. The gas itself, or some other chemical species generated by reaction of the gas with the electrolyte, diffuses through the electrolyte. Upon reaching the working electrode, the electroactive species causes a current to flow which can be measured and related to concentration of the gas to be measured.

The fuel cell type devices generally use sulfuric acid based electrolytes, e.g. typically a 1–8 normal (N) solution, which results in the broad spectrum detection of numerous gases with any particular cell. Selectivity is achieved almost entirely on the basis of controlling the potential imposed between the working and counter electrodes. One problem with this method is that gases having half reactions with similar electrode potentials will cause similar readings. Thus, there is little discrimination between co-existing gases having similar redox couples. Therefore, a gas which is of no interest may interfere with detection of a similar gas. A further problem with the use of a sulfuric acid electrolyte is that sulfuric acid solutions in low concentration are subject to evaporation while more concentrated solutions are hygroscopic and readily absorb moisture from the air. Either condition is undesirable as evaporation requires continuous electrolyte maintenance while absorption eventually causes leakage and failure of the device. These conditions may shorten the service life of the device (typically more than a year) and/or may increase the level of service required during the service life of the device.

The prior art devices utilize high surface area, porous diffusion electrodes bonded to gas permeable membranes. In some cases the electrode is made of a powdered electrode material adhered to the membrane by a polymer binder. Alternatively, the electrode may be sprayed, painted, or sputtered onto the membrane. These methods of manufacture result in a highly porous structure. This porous structure is desired in the prior art to create a large surface area for reaction by virtue of the pores into which solution may diffuse.

The fuel type devices are plagued by high residual current flow as the devices react with air from the ambient and water from the electrolyte. This residual current flow contributes significantly to zero drift and consequently, false alarms in the field. Aside from the substantial costs related to false alarms, worker health and safety is threatened as recurring alarms may be disregarded as false. In addition, since the residual current flow is temperature and humidity dependent, ambient changes in temperature and/or humidity further aggravate zero drift, increasing the frequency of false alarms. A significant residual current also decreases substantially the signal-to-noise ratio and consequently, amplifier gain affects the residual current (noise) as well as the signal. Therefore, use of a high amplifier gain to provide for detection at low concentrations may not be practical. Furthermore, zero and span calibration adjustments become interactive and require several back-and-forth adjustments to be properly set.

Since the fuel cell electrodes are micro-porous and extremely high surface area, they typically demonstrate slow rates of response and recovery due to the length of time required for the gas to diffuse to and from the electrode, respectively. The slow response rate limits the early-warning capability of the device as potentially dangerous situations arise. A long response time also increases proportionately the time and materials required to perform accurate calibrations. Excessively high flow rates are often recommended for gas calibration in an attempt to shorten response times. This creates a condition for calibration which differs greatly from the manner in which the sensor normally responds to gas in the environment. With regard to recovery, saturation effects are often observed with even occasional exposure to high concentrations (several hundred ppm) of gas. The saturation effects arise due to the above described time involved for the gas to diffuse away from the electrode. This means unacceptably long periods of recovery ranging from several hours to several days. The electrode composition may also contribute to poor recovery as various gases react chemically and irreversibly with the electrodes.

A further problem with the prior art device is that the signal decays over time, even in the presence of a constant concentration, due to the build-up of above-described diffusion layer. Thus, after the prior art device rises to a given level, the signal will slowly decay over time, even though the gas concentration remains constant.

The prior art devices have an extremely large surface area due to the porous structure, which results in considerable capacitance. Due to capacitive charging, the prior art devices require long start-up periods. from several hours to days, during which time the signal drifts considerably. Such devices require that the electrodes be shorted together or biased with a small voltage during storage to maintain a ready state. Additionally, capacitive currents result in increased noise during operation.

The prior art electrodes are generally comprised of platinum, gold, silver or ordinary carbon (graphite) all of which show aging effects over time. Irreversible sensitivity loss is coincident with electrode aging and limits the service life of the device. In addition, during the serviceable life of the device, such devices are not rechargeable without complete electrode replacement.

The fuel cell type devices generally require a third or reference electrode to maintain a constant potential at the working electrode. Instability at the counter electrode necessitates this use of a separate reference electrode. This complicates the measurement electronics with potentiostat circuitry which further introduces drift and noise in the signal.

What is needed is a method and apparatus for accurately and reproducibly detecting and quantifying concentrations of specific gases, particularly in the low part per million concentration level. What is further needed is a method and apparatus which exhibits minimal zero drift and high signal-to-noise ratio. What is further needed is a method and apparatus which may be started up immediately after storage and which requires no special storage technique such as electrode shorting or biasing. What is further needed is a method and device which requires no electrolyte maintenance for the service life of the device and in which the electrodes are non-degradable so that the device may easily be recharged after normal service life without replacing the electrodes. The method and apparatus should exhibit fast response and recovery and should be essentially unaffected by occasional exposure to high concentrations of gas. The method and apparatus should exhibit high chemical selectivity to allow for monitoring of specific gases. Further, the method and apparatus should allow for a small size device to enable personal, portable monitoring of toxic gas levels.

SUMMARY OF THE INVENTION

A method and apparatus for detecting gas concentration is disclosed. In a preferred embodiment, an electrochemical device having a working electrode, an electrolyte, and a counter electrode is provided. In one embodiment, an array of working electrodes is provided. Also in one embodiment, the working electrode(s) comprise glassy carbon, or other material, preferably polished to a high polish such that the electrodes are substantially non-porous. Additionally, in a preferred embodiment, the electrolyte comprises a solution containing an alkali metal halide such as lithium bromide and/or potassium bromide. Several specific electrolyte solutions and operating bias voltages are disclosed to provide for detection of various gases with high sensitivity and selectivity. The present invention provides for fast response and recovery time, minimal sensitivity to occasional high concentration, negligible zero drift, and high signal-to-noise ratio. The electrochemical device in the present invention requires no electrolyte maintenance for the full service life of the device, and may easily be recharged after the normal service life without replacing the electrodes.

Additional features and benefits of the present invention will become apparent from the detailed description, figures, and claims set forth below.

BRIEF DESCRIPTION OF THE DRAWINGS

The present invention is illustrated by way of example and not limitation in the accompanying figures in which.

DETAILED DESCRIPTION

A method and apparatus for the detection of gases is disclosed. In the following description, numerous specific details are set forth such as specific materials, reticle patterns, dimensions, etc. in order to provide a thorough understanding of the present invention. It will be obvious, however, to one skilled in the art that these specific details need not be employed to practice the present invention. In other instances, well known materials or methods have not been described in detail in order to avoid unnecessarily obscuring the present invention.

Figure 1:
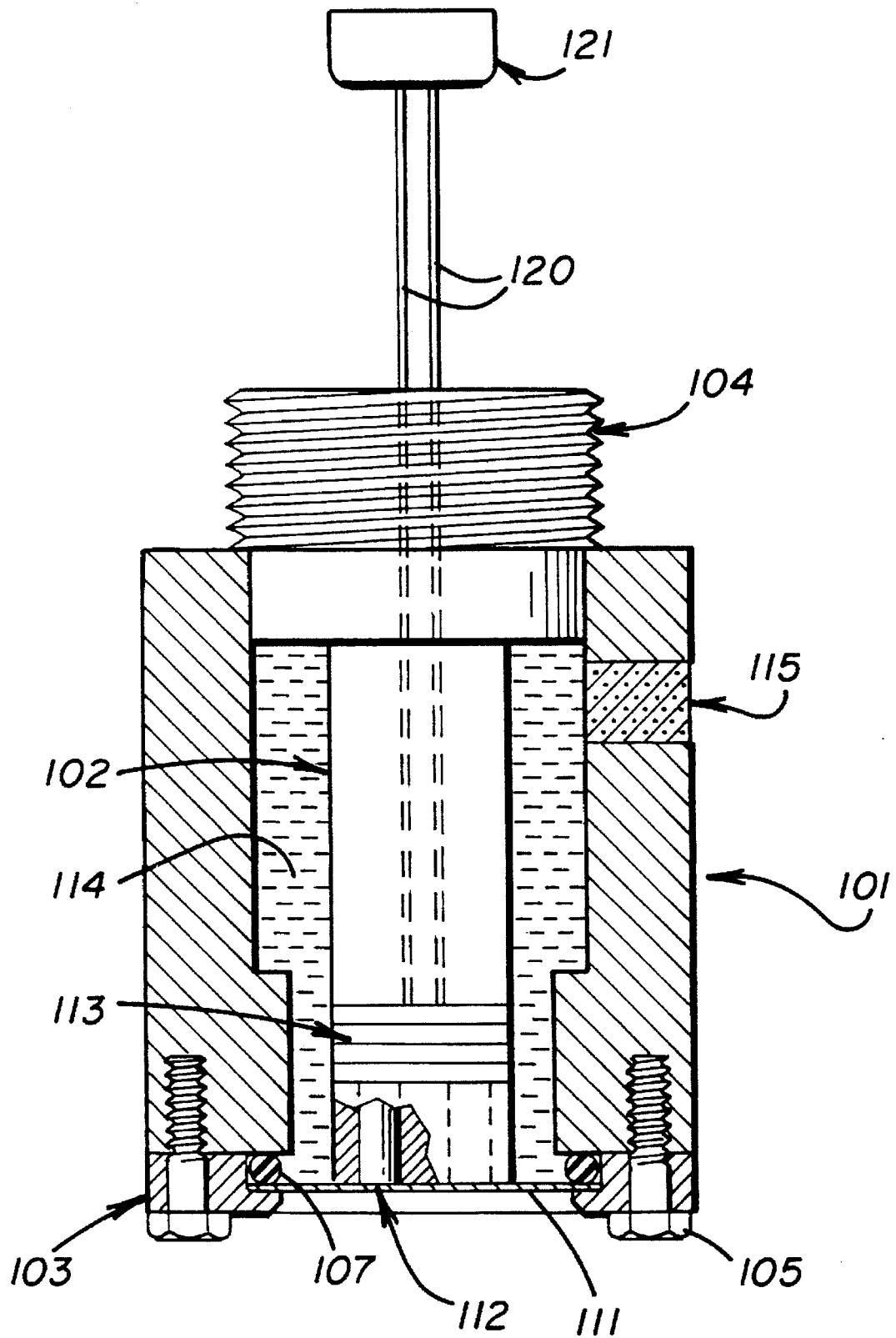
FIG. 1 shows a cross sectional view of a preferred embodiment of a gas sensor according to a preferred embodiment of the present invention.

FIG. 1 shows a currently preferred embodiment of the sensor 100 of the present invention. The sensor 100 comprises housing 101, electrode holder 102, end cap 103 and fitting 104. In a currently preferred embodiment, fitting 104 comprises a ¾ inch NPT fitting. End cap 103 is held to housing 101 by a plurality of screws 105. O-ring 107 is disposed within a recess in end cap 103 and is positioned between housing 101 and membrane 111. The working electrode 112 is disposed on the end of electrode holder 102. In a currently preferred embodiment, a plurality of working electrodes, preferably arranged in a planar array, are utilized. The array of working electrodes will be shown in more detail in FIG. 2. Counter electrode 113 is coiled around electrode holder 102. Vent plug 115 is disposed within an opening in housing 101. In the preferred embodiment, vent plug 115 is made of a porous, hydrophobic material which prevents leakage of the electrolyte but which allows for pressure compensation. In a currently preferred embodiment, housing 101, electrode holder 102, end cap 103, and fitting 104 comprise Ultem 1000™. Counter electrode 113 comprises platinum in a currently preferred embodiment. The screws 105 are made of stainless steel. In a currently preferred embodiment, housing 101 has a height of approximately 1 ½ inches and a diameter of approximately 1 ⅜ inches.

A first wire coupled to each of the working electrodes in electrode array 112, and a second wire coupled to counter electrode 113, passes through the top of electrode holder 102 and through fitting 104 as shown by lead wires 120. Connector 121 couples the sensor 100 to the electronics. Electrolyte solution is disposed in the cavity 114 between the electrode holder 102 and housing 101. Membrane 111 comprises a hydrophobic material such as, for example, Gortex™, Zitex™, or Teflon™ which prevent leakage of the electrolyte but which allow for passage of gas through the membrane 111 into the cavity 114. In a currently preferred embodiment, membrane 111 has a thickness in the range of approximately 0.001 through 0.020 inches thick. In a currently preferred embodiment, electrode holder 102 is filled with a standard electrical resin, available from, for example, General Electric Corporation. The electrical resin acts as an insulator between electrical connections, protects solder connections from moisture corrosion, etc., and prevents wires from being broken or pulled out of the holder 102 during handling.

Figure 2:
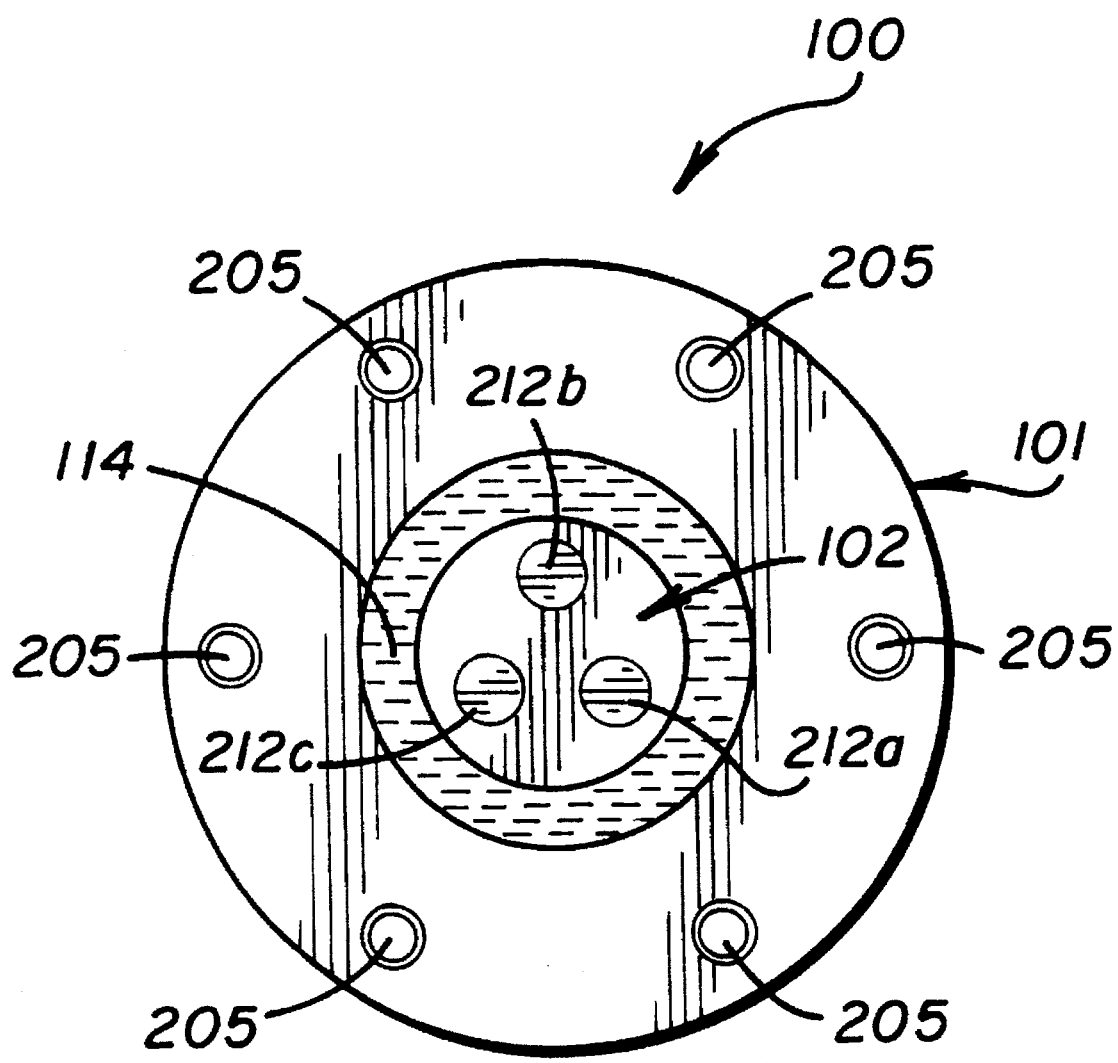
FIG. 2 shows a view of the bottom of the sensor of FIG. 1, illustrating an electrode array in a currently preferred embodiment of the present invention.

FIG. 2 shows an end view of the detector 100. In a currently preferred embodiment, an array 112 of working electrodes is utilized, as mentioned above. In a currently preferred embodiment, working electrode array 112 comprises three working electrodes, 212a, 212b, and 212c. End cap 103, not shown in FIG. 2, comprises a plurality of openings, each of approximately the same diameter as the diameter of the electrodes 212a–212c, and disposed over each of the electrodes 212a–212c. Also as shown, housing 101 comprises screw holes 205 which couple with the screws 105 of FIG. 1 to hold the endcap 103 in place. It will be appreciated that in an alternative embodiment, a single working electrode may be used. Further, in an embodiment using a plurality of working electrodes, the array may contain a fewer or greater number of electrodes as desired. In a preferred embodiment, each of the electrodes 212a–212c comprise glassy carbon, 3 millimeters (mm) in diameter. The electrodes 212a–212c are initially approximately ⅛ inch thick and are placed within holes in the holder 102. Next, the electrodes 212a–212c are surfaced using metalographic grinding and polishing techniques to a high polish. In a currently preferred embodiment, the electrode first undergoes a four stage wet grinding process using successively finer grits of sandpaper, for example, 180, 240, 400, and then 600 grit sandpaper in a currently preferred embodiment. Next, the electrode surface is brought to a mirror finish by polishing first with a 1.0 micron (μ) alumina slurry followed by a 0.05 μ alumina slurry. After polishing, the surfaces of the electrodes 212a–212c are approximately flush with the surface of the bottom end of electrode holder 102 in a currently preferred embodiment, to form a substantially planar array of electrodes. The use of an electrode with a planar surface (i.e., flat surface exposed to the electrolyte solution) creates diffusion conditions that provide for reduced response and recovery times. Further, in the present invention, the response of the device is well defined and repeatable. Although other shapes and/or configurations may be used, use of non-planar electrodes may alter the diffusion to the electrode, which may affect the current versus time behavior as well as the linearity.

For a planar electrode situated in a comparatively large planar insulator, boundary conditions are established for a semi-infinite linear diffusion. As a result, the limiting current, $i_{LIM}$, is defined by the Cottrell equation:

$$i_{LIM} = \frac{nFAD_0^{1/2}C_0}{\pi^{1/2}t^{1/2}} \qquad (1)$$

were n equals the number of electrons generated, F is the Faraday constant, A is the actual active surface area of the electrode, $D_0$ is the diffusion coefficient of the electroactive species, $C_0$ is the concentration of the electroactive species, and t is the time. The time dependence of the current is due to an increase in the diffusion layer thickness, $x_D$, with time as follows:

$$X_d = (\pi D_0 t)^{1/2} \qquad (2)$$

Thus, the thickness of the diffusion layer increases as $t^{1/2}$ for diffusion to a planar electrode in unstirred solution. The above-described diffusion to a large planar electrode is predominantly linear (semi-infinite) with little edge or boundary effects.

However, as the size of the electrode decreases, radial diffusion becomes increasingly significant and affects the overall mode of transport of the electroactive species to the electrode surface. For a smaller electrode, where radial diffusion is significant, equation 1 requires a correction for that radial diffusion and becomes:

$$i_{LIM} = \frac{nFAD_0^{1/2}C_0}{\pi^{1/2}t^{1/2}} \left[ 1 + \frac{b(D_0 t)^{1/2}}{r} \right] \qquad (3)$$

where b is a constant with a value of approximately 2.257 under typical conditions, and r is the radius of the electrode. As can be seen from equation 3, as the correction term dominates, the current quickly becomes independent of time, so that the current does not decay with long term gas exposure to the extent that it decays in the prior art electrode. Thus, the present invention provides essentially time independent steady state currents to provide for accurate steady state monitoring.

As described above, one embodiment of the present invention uses a plurality of electrodes. A benefit of this embodiment is that the use of several electrodes provides high sensitivity since the faradaic current is approximately proportional to the total geometric area of the array (active plus inactive area). The inactive area of the electrodes, e.g., the surface area adjacent to the insulative material of electrode holder 102, contributes to the current due to the contribution of radial diffusion to the electrode. Thus, use of several electrodes provides an increased faradaic current compared with a single, large electrode having the same total active surface area. On the other hand, the capacitive current, which is the current caused by the charging or discharging at the electrode-electrolyte interface, is given by:

$$i_C = C_d A \qquad (4)$$

where A is the area of the electrode, and $C_d$ is the double layer capacitance. Because the capacitive current is proportional to the surface area of the electrode, the use of non-porous electrodes, whose surface area is approximately equal to the small geometric area of the electrode surface, in the present invention results in low capacitive currents. Thus, due to the enhanced signal from an array of electrodes and reduced capacitive charging, the signal-to-noise ratio is increased considerably using an array of smaller, non-porous electrodes. In addition, because the capacitive currents are low, the devices may be started up immediately as the charging process is nearly instantaneous. Thus, the prior art problem of long start-up times with consequent drift in the signal during the start-up period, is avoided.

As mentioned earlier, in one embodiment the working electrodes of the electrode array comprise spectroscopic grade glassy carbon. This material demonstrates exceptional resistance to chemical attack, impermeability to gas and excellent electrical conductivity. Further, the glassy carbon exhibits a high over voltage for hydrogen evolution and for the production of dissolved oxygen. This makes glassy carbon suitable for both cathodic and anodic processes without interfering reactions of air or the electrolyte. The absence of such reactions means negligible background or residual current flow and the associated zero drift. Negligible residual current flow result in a high signal-to-noise ratio, which further enables detection of very low concentrations (e.g., in the 10ths to 100ths of a ppm) which require increased amplifier gain. Glassy carbon also demonstrates increased reversibility for several redox couples. That is, many electrochemical reactions occur easily at glassy carbon electrodes, such that they do not require a large over voltage, which may cause interfering reactions with the electrolyte and/or air.

When the glassy carbon electrodes are prepared as described above, they are virtually non-degradable over time and therefore well-suited to extremely long service life. Because the electrodes do not degrade, sensor recharging involves only the replacement of electrolyte and membrane.

Although one embodiment utilizes a working electrode comprising glassy carbon, or an array of several working electrode with one or more of the array electrodes comprising glassy carbon, other materials including platinum, gold, silver and other forms of carbon such as a graphite may be used in one or more of the working electrodes. The electrode material should be finished to a high polish as described above to make it substantially non-porous. Use of a non-porous electrode, by eliminating the problems associated with diffusion through a porous material, provides for fast response and recovery. Further, although one embodiment of the preferred invention utilizes a counter electrode 113 comprising platinum, the counter electrode may comprise, for example, glassy carbon, platinum, gold, silver and other forms of carbon.

Figure 3:
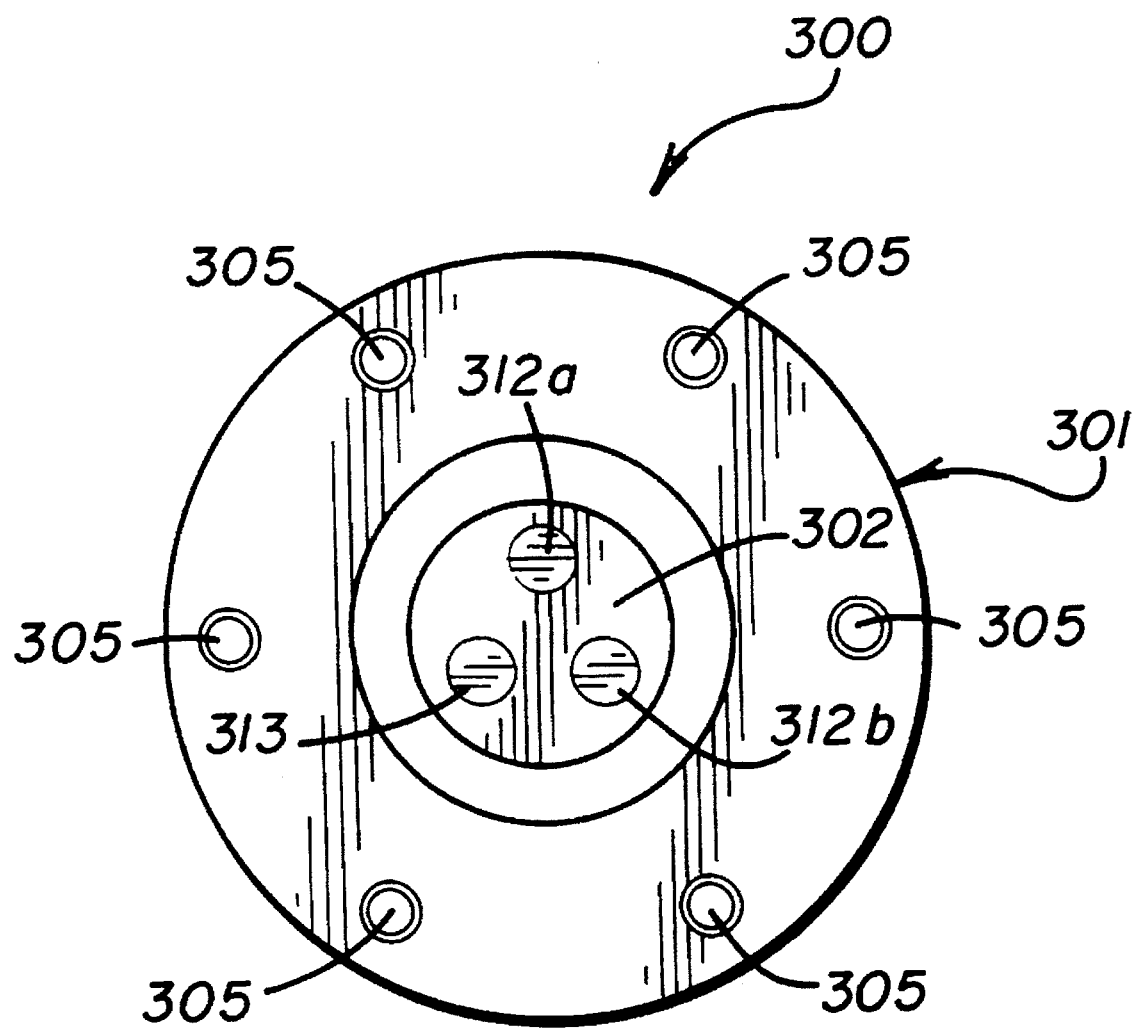
FIG. 3 shows a view of the bottom of a sensor in a further currently preferred embodiment of the present invention.

As a further alternative of the present invention, one or more of the electrodes in the array may constitute the counter electrode. For example, referring now to FIG. 3, the end of a sensor 300 is shown. Sensor 300 is generally similar to sensor 100, except as noted. Sensor 300 comprises housing 301 and electrode holder 302. As shown, housing 301 comprises screw holes 305 which are similar to the screw holes 205 of FIG. 2. In this sensor, electrodes 312a and 312b comprise the working electrodes while electrode 313 comprises the counter electrode. Again, any of the electrodes can be made of any of the materials described previously. In further embodiments, additional counter and/or working electrodes may be provided. For example, three electrodes such as electrodes 212a–212c of FIG. 2 may surround a counter electrode such that there are four electrodes in the planar array. In any such arrangement wherein one or more of the counter electrodes is disposed in the planar array, separate leads are maintained to the counter and working electrodes such that a first lead is coupled in parallel to each of the counter electrodes and a second lead is coupled in parallel to each of the working electrodes.

By placing the counter electrode in the array, the device may be miniaturized with the electrolyte volume limited to a few drops. For example, a device having the counter electrode in the array may have an overall height of approximately ¼ inch or less. Obviously, further miniaturization in the housing and electrode holder may provide for further down-sizing. Use of this packaging is advantageous for use of the device in personal monitors.

In the present invention, the electrolyte is formulated such that a chemical reaction in the electrolyte is directly coupled to the signal producing electrochemical process, thereby providing excellent selectivity. Therefore, only compounds capable of reacting specifically with the electrolyte can generate the electroactive species and, in turn, generate current flow through the cell. Thus, as will be described in more detail below, the electrolyte composition varies with the type of gas detected and is further formulated to avoid problems of evaporation, freezing and absorption of moisture. Furthermore, the electrolyte solutions described below do not rely on reactions involving oxygen at the counter electrode, as is often the case of prior art devices. Therefore, the sensors of the present invention can be used to detect gases present in an inert ambient. In addition, since the electrolyte solutions of the present invention do not produce a reaction which consumes or alters the counter electrode, stability at the counter electrode is maintained so that a third, reference electrode is not required in the present invention.

In general, the electrolytes described below comprise a sufficiently concentrated solution of hydrated spectator ions such as lithium (Li) or potassium (k), which ensures a low vapor pressure and correspondingly low evaporation rate and freezing point. The electrolytes described below have a concentration of an alkali metal halide, such as, for example, a lithium or potassium salt such that equilibrium is substantially established between the water in the cell and water vapor in the air. The electrolytes described below have been found to be effective in a relative humidity range of at least approximately 5% through 95%. Although one or more specific alkali metal halides are described in conjunction with use for sensing various gases, it will be appreciated that one or more of several such components, including lithium bromide (LiBr), potassium bromide (KBr), lithium chloride (LiCl), sodium bromide (NaBr), sodium chloride (NaCl), potassium chloride (KCl) or other similar compound may be utilized. Some adjustment to the relative percentage of one or more components may be necessary when substituting one or more metal halide for one or more of the metal halides in the compositions described below.

The use of the non-porous, planar electrodes described above in combination with the electrolytes described below provides for rapid recovery from occasional exposure to high concentrations. Therefore, following a high concentration from, for example, a substantial leakage of gas, the sensor will reliably track the recovery of the environment without suffering significant saturation effects. Further, the response of the sensor is very fast, even after long periods of zero or very low concentrations of the gas to be detected. For example, the embodiments described below typically reach 90% of the final reading in less than 30 seconds. Similarly, the recovery is very fast. For example, in situations where the measured gas drops from a given concentration to a negligible concentration, the sensor reading drops to approximately 10% of the given value in typically less than approximately 15 seconds.

In one embodiment of the present invention, a sensor designed to detect chlorine, fluorine, and bromine may use an aqueous or partially aqueous (i.e., having an organic solvent for example) electrolyte comprising a bromide ion. In one embodiment the electrolyte preferably comprises 30% through 50% by weight of potassium bromide (KBr) or a combination of KBr and lithium bromide (LiBr). The partially aqueous electrolyte additionally comprises 10% through 40% by weight ethylene glycol, glycerin, or combination of ethylene glycol and glycerin in a currently preferred embodiment. Further in a currently preferred embodiment, the operating bias voltage applied between the working electrodes and counter electrode is in the range of approximately −150 through −250 millivolts (mV). As used herein, the stated polarity of the operating bias voltage is at the working electrode.

In a sensor designed to detect hydrogen sulfide ($H_2S$), the electrolyte comprises approximately 0.4 through 0.8% by weight copper sulfate ($CuSO_4.5H_2O$) and approximately 30% through 50% by weight LiBr in a preferred embodiment. Further, the electrolyte pH is adjusted below 3 with a strong mineral acid such as hydrochloric acid (HCl) or sulfuric acid ($H_2SO_4$). In a preferred embodiment, an operating bias voltage in the range of approximately −20 through −60 mV is applied between the electrodes.

In a sensor designed to detect chlorine dioxide ($ClO_2$), nitrogen dioxide ($NO_2$), ozone ($O_3$), and hydrogen peroxide ($H_2O_2$), the electrolyte comprises approximately 30% through 50% by weight LiBr. The pH of the electrolyte is adjusted below approximately 3 with HCl or phosphoric acid ($H_3PO_4$). In a preferred embodiment, the operating bias voltage between the working and counter electrodes is in the range of approximately −150 through −250 mV.

In a sensor designed to detect hydrogen chloride (HCl), hydrogen fluoride (HF), hydrogen bromide (HBr), sulfur dioxide ($SO_2$), nitric acid ($HNO_3$) and sulfuric acid ($H_2SO_4$), an aqueous or partially aqueous solution comprising approximately 30% through 50% by weight KBr or a combination of KBr and LiBr is used. In addition, the electrolyte also comprises approximately 0.4% through 1.0% by weight potassium bromate ($KBrO_3$) in a preferred embodiment. In an embodiment using a partially aqueous electrolyte, the electrolyte additionally contains approximately 10% through 40% by weight ethylene glycol, glycerin, or a combination of ethylene glycol or glycerin. In a preferred embodiment, the operating bias voltage between the working and counter electrodes is in the range of approximately −150 through −250 mV.

In a further preferred embodiment of the present invention, a sensor designed to detect ammonia ($NH_3$) gas utilizes an electrolyte that comprises approximately 0.3% through 0.5% by weight $CuSO_4 \cdot 5H_2O$, and approximately 30% through 50% by weight LiBr. In a preferred embodiment the pH is adjusted to 4 using a standard, off-the-shelf buffer. Additionally, in a preferred embodiment, the electrolyte comprises approximately 0.6% through 0.8% by weight tris amine buffer. Also in a currently preferred embodiment, the operating bias voltage is in the range of approximately +40 through −100 mV.

In a sensor designed to detect hydrogen cyanide (HCN), the electrolyte comprises in the range of approximately 0.3% through 0.5% by weight $CuSO_4 \cdot 5H_2O$ and in the range of approximately 30% through 50% by weight LiBr. In addition, in a preferred embodiment, the electrolyte also comprises approximately 0.3% through 0.6% by weight tris amine buffer. The operating bias voltage between the working and counter electrodes is in the range of approximately −20 through −50 mV.

Figure 4:
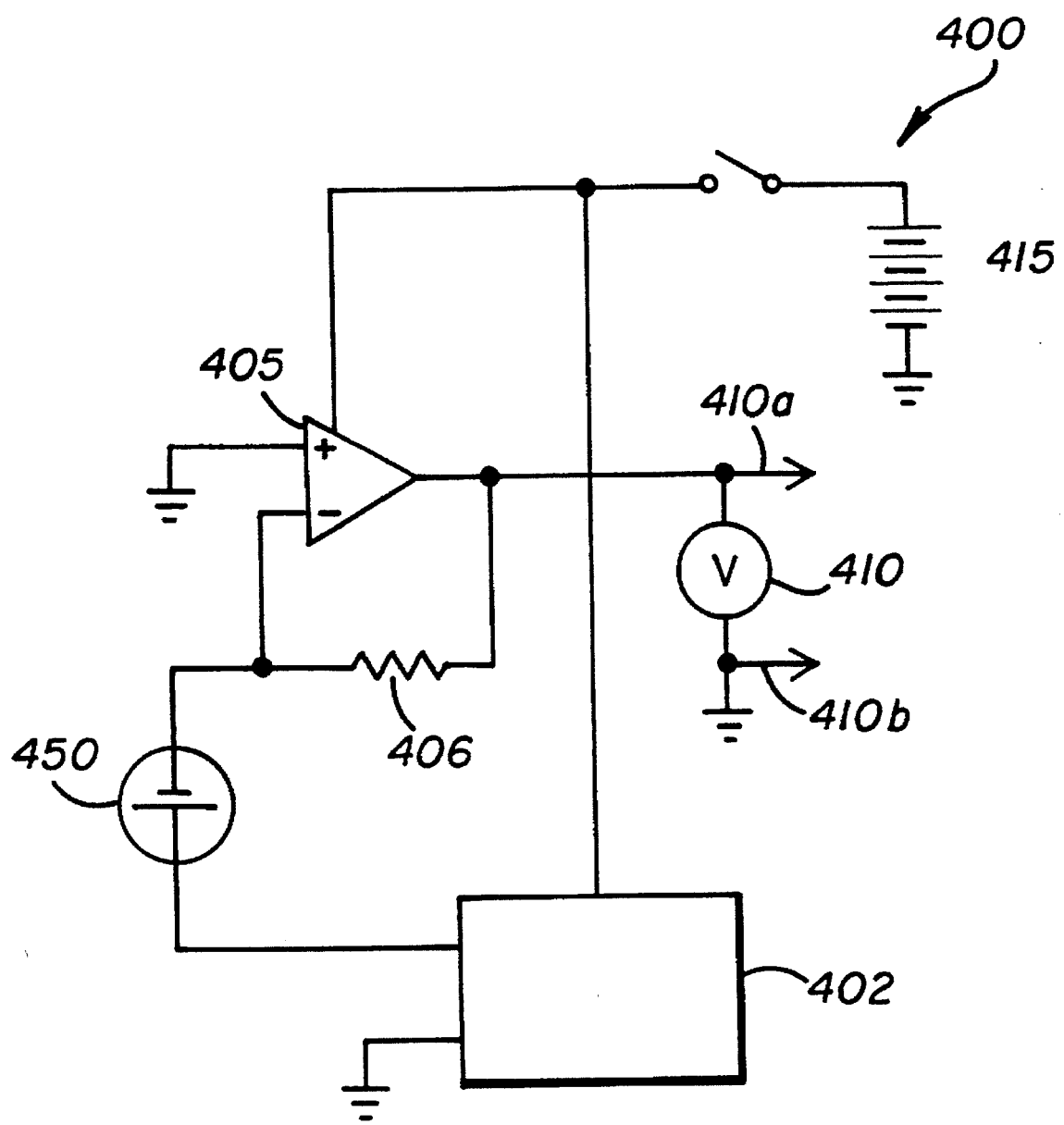
FIG. 4 shows a circuit which may be used to obtain an output voltage from the sensor of the present invention.

As described earlier, the presence of a toxic gas which a sensor is designed to detect will produce a current proportional to the concentration of the toxic gas. FIG. 4 illustrates circuit 400 that may be used to obtain a usable voltage output which can be related to concentration. Circuit 400 of FIG. 4 also provides the appropriate operating bias voltage. Adjustable bias voltage supply 402 supplies the operating bias voltage across the electrodes of sensor 450, which may be any of the sensors of the present invention. As described above, each sensor has a range of preferable operating bias voltage. In general, the operating bias voltage which supply 402 must provide is typically within the range of approximately ±300 mV. For any type of sensor, an optimum bias voltage is determined by testing the output over a range of concentrations, at a variety of bias voltages. A voltage is selected which shows high sensitivity and linearity. Additionally, the sensor must be relatively insensitive to small changes in the bias voltage, so that if, for example, a sensor exhibits a threshold voltage, the operating voltage is set sufficiently removed from the threshold voltage such that the sensitivity and linearity will not change due to any changes in the operating voltage. Once an optimum voltage is determined for a given type of sensor, supply 402 is set to that value for all sensors of the same type. The optimum bias voltage for the specific sensors described above is typically within the range of voltages given for each sensor.

Still referring to FIG. 4, the current produced by the cell is converted to a readable voltage by use of operational amplifier 405, and feedback resistor 406, which produce a linear output voltage ($V_{OUT}$) according to the formula:

$$V_{out} = I_{in} \times R_f \qquad (5)$$

where $I_{in}$ is the current produced by the sensor 450, and $R_f$ is the resistance of the feedback resistor 406. If units of microamperes are used for $I_{in}$, and megohms for $R_f$, equation 5 gives $V_{OUT}$ in volts. Typically, the current $I_{in}$ for full scale gas concentration is less than 10 microamperes. The output voltage, $V_{OUT}$, is read on voltage meter 410, which may be calibrated to indicate gas concentration directly. Since the amplifier 405 cannot produce an output voltage higher than that of power supply 415, the feedback resistor has a value such that the full scale output voltage at the voltage meter 410 is less than the voltage of power supply 415, which may be, for example, a battery. For example, if a sensor produces a current ranging from 0–4 microamperes over its full sensing range, and power supply 415 is a 5 volt supply, the maximum $R_f$ value would be 1.25 megohms since 4 microamperes multiplied by 1.25 megohms equals 5 volts. If desired, the same voltage read by voltage meter 410 may be routed via leads 410a and 410b to external readout or data logging devices such as voltmeters, recorders, or data acquisition equipment.

In the present invention, a planar array of comparatively small working electrodes are employed. Additionally, in a preferred embodiment, the electrode material is made to be substantially non-porous. The electrode of the present invention provides for fast response since radial diffusion to the electrode surface is significant and since the present invention does not require the time consuming process of diffusion through a microporous structure. Additionally, the present invention provides fast recovery as saturation effects are avoided. Also, since there is little or no diffusion through the material of the working electrode, residual currents from diffusion related effects are minimized. Further, the present invention achieves a high signal-to-noise ratio allowing for detection over a range of concentrations typically spanning several times the threshold limit value. In a preferred embodiment of the present invention, one or more of the working electrodes comprises glassy carbon which is resistant to chemical attack, impermeable to gas and highly conductive. The glassy carbon substantially prevents interfering reactions of air or the electrolyte. In the present invention, electrolytes showing excellent selectivity to specific gases to be detected have been described. The electrolyte ensures that the chemical reaction is directly coupled to the signal producing electrochemical process so that the current flow detected is directly proportional to the amount of gas present with little interference from unrelated gases. Additionally, the electrolytes avoid the problem of evaporation, freezing, and absorption of moisture from the atmosphere. Because there is no or only minimal residual current flow from capacitive changing of the electrode, diffusion within the electrode, interfering reactions of air or the electrolyte, or interference with other gases, the present invention provides for negligible background noise and negligible zero drift.

Thus, a method and apparatus for the detection of gases has been described. Although specific embodiments, including specific equipment, parameters, methods, dimensions, structures, and materials have been described, various modifications to the disclosed embodiments will be apparent to one of ordinary skill in the art upon reading this disclosure. Therefore, it is to be understood that such embodiments are merely illustrative of and not restrictive on the broad invention and that this invention is not limited to the specific embodiments shown and described.

What is claimed is:

1. An electrochemical cell for detecting chlorine, fluorine and bromine gas in ambient air comprising:

a platinum counter electrode;

a plurality of glassy carbon working electrodes having exposed surfaces finished to a high polish;

an electrolyte comprising 30% through 50% by weight potassium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately −150 through −250 millivolts applied between said counter electrode and said plurality of working electrodes to initiate electrochemical reactions only with the chlorine, fluorine and bromine gas to be detected.

2. The electrochemical cell of the claim 1 wherein the glassy carbon working electrodes are arranged to form an array.

3. The electrochemical cell of claim 2 wherein said counter electrode is disposed within said array.

4. The electrochemical cell of claim 1 wherein the number of working electrodes is three.

5. The electrochemical cell of claim 1 wherein the electrolyte comprises 30% through 50% by weight of a combination of potassium bromide and lithium bromide.

6. The electrochemical cell of claim 1 wherein the electrolyte comprises 30% through 50% by weight lithium bromide.

7. The electrochemical cell of claim 1 wherein the electrolyte is partially aqueous and comprises 10% through 40% by weight ethylene glycol.

8. An electrochemical cell for detecting hydrogen sulfide gas in ambient air comprising:

a platinum counter electrode, a plurality of glassy carbon working electrodes having exposed surfaces finished to a high polish;

an electrolyte comprising approximately 0.4% through 0.8% by weight copper sulfate and approximately 30% through 50% by weight lithium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately −20 through −60 millivolts applied between said counter electrode and said plurality of working electrodes to initiate electrochemical reactions only with the hydrogen sulfide gas to be detected.

9. The electrochemical cell of claim 8 wherein the electrolyte has a pH adjusted below 3.

10. The electrochemical cell of claim 9 wherein the pH is adjusted below 3 with hydrochloric acid.

11. The electrochemical cell of claim 9 wherein the pH is adjusted below 3 with sulfuric acid.

12. An electrochemical cell for detecting chlorine dioxide, nitrogen dioxide, ozone and hydrogen peroxide gas in ambient air comprising:

a platinum counter electrode;

a plurality of glassy carbon working electrodes having exposed surfaces finished to a high polish;

an electrolyte comprising approximately 30% through 50% by weight lithium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately −150 through −250 millivolts applied between said counter electrode and said plurality of working electrodes to initiate electrochemical reactions only with the chlorine dioxide, nitrogen dioxide, ozone and hydrogen peroxide gas to be detected.

13. The electrochemical cell of claim 12 wherein the electrolyte has a pH adjusted below 3.

14. The electrochemical cell of claim 13 wherein the pH is adjusted below 3 with hydrochloric acid.

15. The electrochemical cell of claim 13 wherein the pH is adjusted below 3 with phosphoric acid.

16. An electrochemical cell for detecting hydrogen chloride, hydrogen fluoride, hydrogen bromide, sulfur dioxide, nitric acid and sulfuric acid gas in ambient air comprising:

a platinum counter electrode;

a plurality of glassy carbon working electrodes having exposed surfaces finished to a high polish;

an electrolyte comprising approximately 0.4% through 1.0% by weight potassium bromate and approximately 30% through 50% by weight potassium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately −150 through −250 millivolts applied between said counter electrode and said plurality of working electrodes to initiate electrochemical reactions only with hydrogen chloride, hydrogen fluoride, hydrogen bromide, sulfur dioxide, nitric acid and sulfuric acid gas to be detected.

17. The electrochemical cell of claim 16 wherein the electrolyte comprises 30% through 50% by weight of a combination of potassium bromide and lithium bromide.

18. The electrochemical cell of claim 16 wherein the electrolyte is partially aqueous and comprises 10% through 40% by weight ethylene glycol.

19. An electrochemical cell for detecting ammonia in ambient air comprising:

a platinum counter electrode;

a plurality of glassy carbon working electrodes having exposed surfaces finished to a high polish;

an electrolyte comprising approximately 0.3% through 0.5% by weight copper sulfate, approximately 0.6% through 0.8% by weight tris amine buffer, and approximately 30% through 50% by weight lithium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately +40 through −100 millivolts applied between said counter electrode and said plurality of working electrodes to initiate electrochemical reactions only with the ammonia gas to be detected.

20. The electrochemical cell of claim 19 wherein the electrolyte has a pH adjusted below 4.

21. An electrochemical cell for detecting hydrogen cyanide gas in ambient air comprising:

a platinum counter electrode;

a plurality of glassy carbon working electrodes having exposed surfaces finished to a high polish;

an electrolyte comprising approximately 0.3% through 0.5% by weight copper sulfate, approximately 0.3% through 0.6% by weight tris amine buffer, and approximately 30% through 50% by weight lithium bromide in operative contact with said counter electrode and said exposed surfaces of said working electrodes;

a gas permeable hydrophobic membrane enclosing said counter electrode, said plurality of working electrodes, and said electrolyte within said cell; and means providing a fixed potential of approximately −20 through −50 millivolts applied between said counter electrode and said plurality of working electrodes to initiate electrochemical reactions only with the hydrogen cyanide gas to be detected.

22. A method of detecting ammonia gas in ambient air with an electrochemical cell comprising the steps of:

providing a platinum counter electrode;

providing a plurality of glassy carbon working electrodes having surfaces finished to a high polish;

operatively contacting said counter electrode and said plurality of exposed surfaces of said working electrodes with an electrolyte comprising approximately 0.3% through 0.5% by weight copper sulfate, approximately 0.6% through 0.8% by weight tris amine buffer, and approximately 30% through 50% by weight lithium bromide;

enclosing said counter electrode, said plurality of working electrodes, and said electrolyte within said cell by a gas permeable hydrophobic membrane; and applying a fixed potential of approximately +40 through −100 millivolts between said counter electrode and said plurality of working electrodes sufficient to initiate electrochemical reactions only with the ammonia gas to be detected.

23. A method of detecting chlorine, fluorine and bromine gas in ambient air with an electrochemical cell comprising the steps of:

providing a platinum counter electrode;

providing a plurality of glassy carbon working electrodes having surfaces finished to a high polish;

operatively contacting said counter electrode and said plurality of exposed surfaces of said working electrodes with an electrolyte comprising 30% through 50% by weight potassium bromide;

enclosing said counter electrode, said plurality of working electrodes, and said electrolyte within said cell by a gas permeable hydrophobic membrane; and applying a fixed potential of approximately −150 through −250 millivolts between said counter electrode and said plurality of working electrodes sufficient to initiate electrochemical reactions only with the chlorine, fluorine and bromine gas to be detected.

24. A method of detecting hydrogen chloride, hydrogen fluoride, hydrogen bromide, sulfur dioxide, nitric acid and sulfuric acid gas in ambient air with an electrochemical cell comprising the steps of:

providing a platinum counter electrode;

providing a plurality of glassy carbon working electrodes having surfaces finished to a high polish;

operatively contacting said counter electrode and said plurality of exposed surfaces of said working electrodes with an electrolyte comprising approximately 0.4% through 1.0% by weight potassium bromate and approximately 30% through 50% by weight potassium bromide;

enclosing said counter electrode, said plurality of working electrodes, and said electrolyte within said cell by a gas permeable hydrophobic membrane; and applying a fixed potential of approximately −150 through −250 millivolts between said counter electrode and said plurality of working electrodes sufficient to initiate electrochemical reactions only with the hydrogen chloride, hydrogen fluoride, hydrogen bromide, sulfur dioxide, nitric acid and sulfuric acid gas to be detected.

* * * * *